United States Patent [19]

Hess

[11] Patent Number: 4,690,148
[45] Date of Patent: Sep. 1, 1987

[54] SURFACE MAPPING ELECTRODE SETS
[75] Inventor: Stanley R. Hess, Miami, Fla.
[73] Assignee: Cordis Corporation, Miami, Fla.
[21] Appl. No.: 5,314
[22] Filed: Jan. 16, 1987

Related U.S. Application Data

[63] Continuation of Ser. No. 650,192, Sep. 13, 1984, abandoned.

[51] Int. Cl.⁴ .................................................. A61B 5/04
[52] U.S. Cl. ...................... 128/639; 128/644; 128/798
[58] Field of Search .................... 128/639–644, 128/419 P, 783–786, 789, 798, 802

[56] References Cited

U.S. PATENT DOCUMENTS

| | | | |
|---|---|---|---|
| 4,144,889 | 3/1979 | Tyers et al. | 128/419 P X |
| 4,323,081 | 4/1982 | Wiebusch | 128/419 P X |
| 4,354,509 | 10/1982 | Strahwald et al. | 128/639 X |
| 4,365,634 | 12/1982 | Bare et al. | 128/798 X |
| 4,381,789 | 5/1983 | Naser et al. | 128/798 |
| 4,407,303 | 10/1983 | Akerstrom | 128/786 X |
| 4,510,939 | 4/1985 | Brenman et al. | 128/639 |
| 4,522,212 | 6/1985 | Gelinas et al. | 128/419 P X |
| 4,537,198 | 8/1985 | Corbett | 128/639 |
| 4,628,937 | 12/1986 | Hess et al. | 128/642 |

FOREIGN PATENT DOCUMENTS 2709668 9/1978 Fed. Rep. of Germany ...... 128/639
1523263 8/1978 United Kingdom ................ 128/642

OTHER PUBLICATIONS

Johnston et al.; "Body Tissue Transducer"; *IBM Technical Disclosure Bulletion*, vol. 6, No. 8, 1-1964, pp. 13-14.

Primary Examiner—Kyle L. Howell
Assistant Examiner—Angela D. Sykes
Attorney, Agent, or Firm—Lockwood, Alex, Fitzgibbon & Cummings

[57] ABSTRACT

A surface mapping electrode set assembly is provided which includes a plurality of insulated, elongated wires, each of which terminates at a distal end head portion of the assembly. The electrodes of the mapping electrode set are generally arcuate portions of the wires, each generally arcuate electrode projecting through a slit in the administration surface of the assembly while the distal tip portion of the wire remains beneath such administration surface.

15 Claims, 14 Drawing Figures

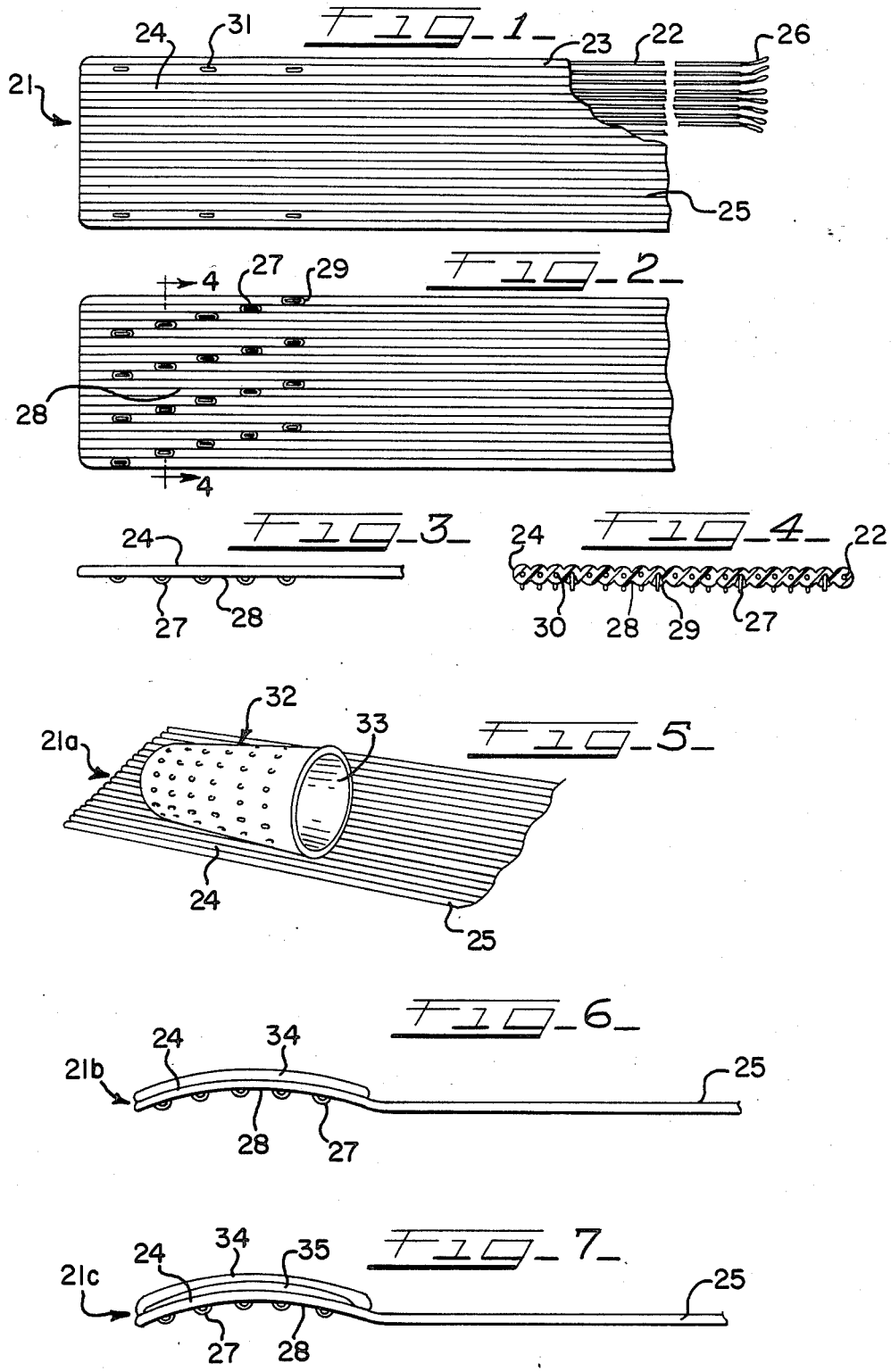

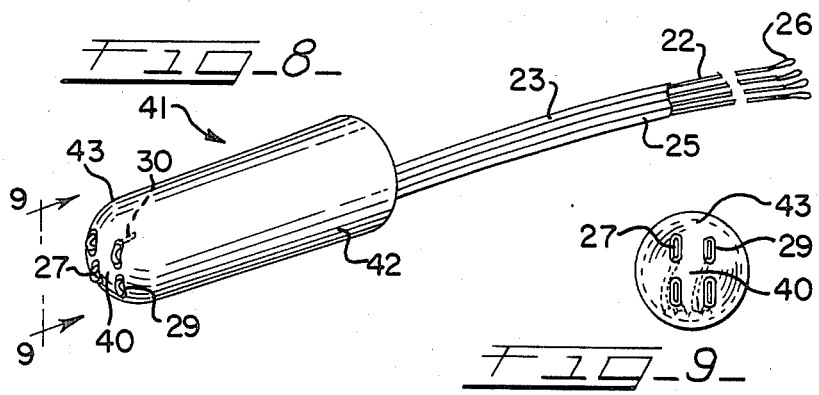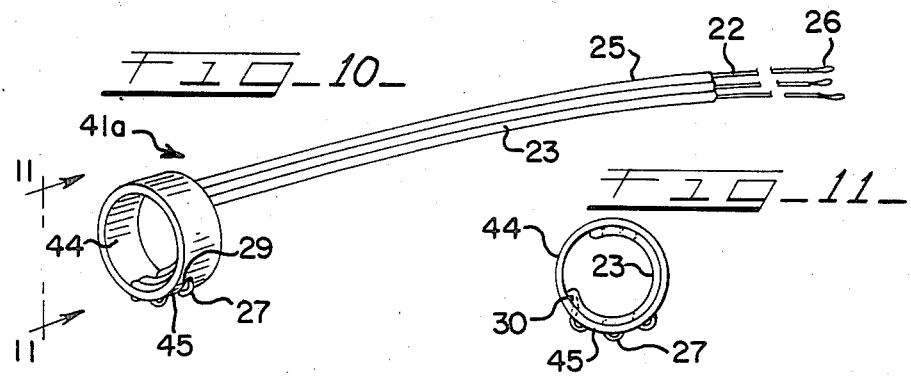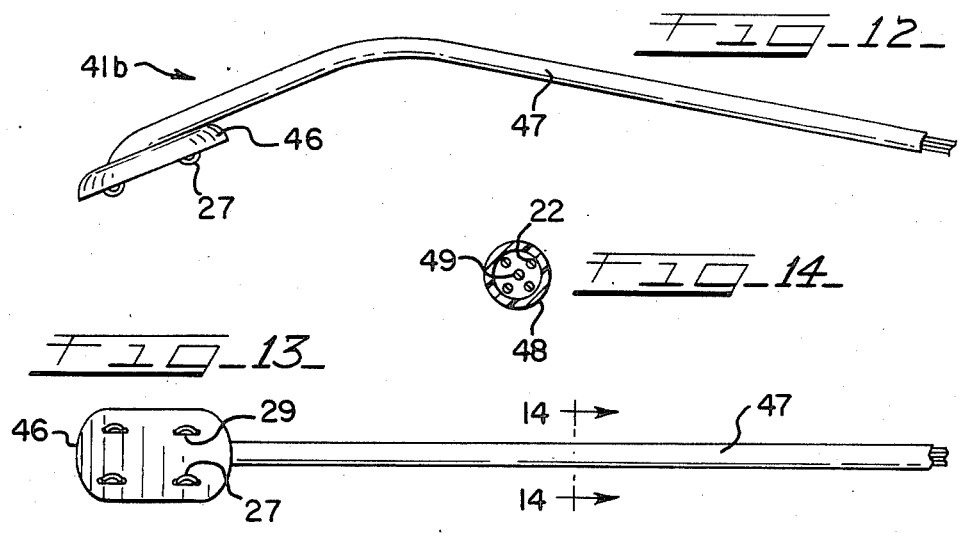

SURFACE MAPPING ELECTRODE SETS

This application is a continuation of application Ser. No. 650,192, filed Sept. 13, 1984, now abandoned.

BACKGROUND OF THE INVENTION

This invention generally relates to cardiac mapping, more particularly to surface mapping electrode sets and the making of same, which surface mapping electrode sets are suitable for conducting epicardial and/or endocardial mapping. Electrode sets according to this invention include an administration portion or head, a plurality of insulated wires that are positioned generally longitudinally adjacent to each other and that each have a distal end embedded within the head portion which has an administration surface. Making the electrode set includes slitting the insulation of the administration surface at locations above the electrodes, and each portion of each electrode that is exposed by each slit is pulled or bent outwardly to form a generally arcuate electrode that projects through the slit. The plurality of thus formed generally arcuate electrodes form a set of electrodes that are suitable for mapping of cardiac surfaces.

Mapping electrode sets for epicardial and endocardial mapping of heart signals have been provided in the past. Typically, these mapping electrode sets are utilized during cardiac surgery in order to sense the cardiac signal and report it to the surgical team through appropriate display and/or printout devices. The surgical team may observe the reported data and immediately utilize the data in connection with a surgical procedure, or the data may be collected for subsequent analysis. Such mapping involves timing that is based upon the leading edge of an excitation wave through conductive tissue of the heart. Generally, mapping procedures include the induction of tachycardia while the mapping electrode is positioned on the cardiac tissue by the surgeon.

Various structures of mapping electrode sets have been developed or proposed. Many of these structures require somewhat complicated and difficult fabrication techniques. Also, these mapping electrode sets typically include electrodes that are the distal tips of the wires which transmit the signals to the data receiving unit, which distal tips project beyond the administration surface of the mapping device. Often, these projecting distal tips of the electrode wires must be modified in some manner in order to provide a suitable electrode. For example, the distal tips may have a very small diameter or have somewhat sharp edges, both of which increase the possibility of penetration thereby of heart tissue or of trauma to the heart.

Techniques are available for modifying such wire tips in order to minimize the possibility of heart penetration or trauma. Included are means for modifying the configuration of the wire tip. Often, because the wires used in mapping devices are exceptionally thin, efforts to minimize heart tissue penetration and trauma most advantageously include increasing the size of the tip, such as by adding a blunt or spherical member thereto or by reshaping the tip. One type of acceptable procedure is to subject the wire tip to inert gas shielded arc welding, particularly inert gas welding that utilizes a non-consumable tungsten electrode, this procedure being known as TIG.

Another important consideration regarding mapping electrode sets is that they are disposable. Accordingly, economic factors strongly favor the use of components and procedures that minimize or decrease the cost of the mapping electrode set. It is also important that the mapping electrode set provide the surgeon with the ability to accurately position the electrodes at a desired location on the outside or inside surface of the heart so that the surgeon can very accurately determine the precise location of the blocked area of the tissue to be surgically removed or treated. Surface mapping electrode sets should therefore be easily maneuverable by the fingers of the surgeon.

SUMMARY OF THE INVENTION

These various needs and desirable attributes are achieved by the present invention which provides a surface mapping electrode set assembly that includes a plurality of insulated wires which are positioned generally adjacent to each other and which have distal end tips that are embedded within a head portion of the assembly such that these tips are beneath the administration surface of the assembly. Each electrode for surface mapping is formed from a section of the wire that is generally proximally spaced from the embedded distal tip, each such section projecting through a slit in the administration surface. Various numbers of electrodes can be provided on the assembly in this manner, and the wires provide electrical communication between the electrode and the signal recording or display device. Each surface mapping electrode set exhibits some degree of maneuverability and bendability in order to provide the surgeon with a device that can be positively and firmly positioned onto the surface of most portions of the heart.

It is accordingly a general object of the present invention to provide an improved surface mapping electrode set and method of making same.

Another object of the present invention is to provide an improved surface mapping electrode set that is economical and easily manufactured.

Another object of the present invention is to provide an improved surface mapping electrode set that includes electrodes which are structured to minimize the likelihood of their penetration into heart tissue or of heart trauma associated therewith.

Another object of the present invention is to provide an improved surface mapping electrode set assembly that provides generally arcuate electrodes along the administration surface thereof.

Another object of this invention is to provide an improved mapping electrode set assembly and method that can be readily manufactured with a variety of different numbers of electrodes.

BRIEF DESCRIPTION OF THE DRAWINGS

These and other objects of the present invention will be apparent from the following description of the invention, taken in conjunction with the accompanying drawings, wherein:

FIG. 1 is a top plan view of a basic embodiment of this invention, which utilizes a ribbon electrode assembly;

FIG. 2 is a bottom plan view of the embodiment illustrated in FIG. 1;

FIG. 3 is an elevational view of the embodiment illustrated in FIG. 1;

FIG. 4 is an enlarged cross-sectional view along the line 4—4 of FIG. 2;

FIG. 5 is a perspective view of an embodiment similar to that of FIGS. 1 through 4, including the additional feature of a bendable finger sleeve;

FIG. 6 is an elevational view of another embodiment generally including the features of FIGS. 1 through 4, this embodiment including a bendable support secured to the back of the head portion;

FIG. 7 is an elevational view of another embodiment similar to that illustrated in FIG. 6, with the backing including a reinforcement member;

FIG. 8 is an illustration of another embodiment of the surface mapping electrode set that is especially suitable for endocardial mapping and which includes a finger-receiving sleeve;

FIG. 9 is an end view of the embodiment illustrated in FIG. 8;

FIG. 10 is a perspective view of an embodiment generally along the lines of that of FIGS. 8 and 9 and which includes a finger ring;

FIG. 11 is an end view of the embodiment illustrated in FIG. 10;

FIG. 12 illustrates another embodiment that includes a bendable shaft that maintains its bent configuration to facilitate precise endocardial placement thereof;

FIG. 13 is a bottom plan view of the embodiment of FIG. 12; and

FIG. 14 is a sectional view along the line 14—14 of FIG. 13.

DESCRIPTION OF THE PREFERRED EMBODIMENTS

The surface mapping electrode set assembly of FIGS. 1 through 4 is generally designated as 21. This electrode set assembly is made from a length of so-called ribbon wire. A ribbon wire includes a plurality of elongated wires 22 that are generally longitudinally adjacent to each other and that are encased within and insulated from each other by a flexible polymeric sheath 23. Sheath 23 generally encapsulates and closely conforms to each of the elongated wires 22. The surface mapping electrode set assembly 21 includes a heat portion 24 and a handle portion 25 of the polymeric sheath 23. Each wire 22 is attached at its proximal end to a connector 26 for providing suitable electrical engagement with a monitoring and/or data recording device (not shown).

With more particular reference to the head portion 24 of the surface mapping electrode set 21, such includes a plurality of generally arcuate electrodes 27. In the illustrated embodiment, a total of twenty such generally arcuate electrodes 27 are shown, and a greater or fewer number of electrodes are possible depending upon the particular size of mapping surface that is desired. Each electrode 27 projects beyond the administration surface 28 of the head portion 24 through slits 29 in the administration surface 28.

Preferably, each of the generally arcuate electrodes 27 is formed by the following procedure. A slit 29 is made in the administration surface 28 at a location immediately above the selected wire. This slit is made at a location on the administration surface 28 that is spaced from the distal tip 30 of the elongated wire 22. By so positioning the slit, the distal tip 30 of each wire 22 remains under the administration surface 28 and embedded within the polymeric sheath 23. At this stage, the portion of the elongated wire 22 that is beneath each slit 29 is somewhat exposed, but typically does not protrude through the slit 29. Accordingly, the procedure for making the generally arcuate electrodes 27 includes a subsequent step of pulling, such as with a fine hook-like tool, the portion of the elongated wire 22 that is beneath the slit 29. Such pulling continues until this portion of wire is pulled through the slit 29, which pulling shapes such section of the elongated wire 22 into the generally arcuate electrode 27.

Regarding the surface mapping electrode set assembly 21 of this embodiment, the ribbon wire comprised of the elongated wires 22 embedded within the polymeric sheath 23 provides a structure that is easily formed or shaped by the fingers of a person on the surgical team. Such ribbon wire is not so flexible as to be limp, but provides enough bendability to permit generally arcuate bending to the extent that the ribbon wire could take on a circular configuration of no smaller than approximately one one-half inch in diameter. With these properties, it is possible to shape the administration surface in order to approximate the shape of most surfaces of the heart. This flexibility of the ribbon wire also permits bending of the handle portion 25 as necessary in order to maneuver and manipulate the surface mapping electrode set assembly 21 in order to conveniently orient the assembly 21 with respect to the patient. If desired, suture holes 31 may be included through the head portion 24 of this or other embodiments in order to permit the surgeon to temporarily securely position the surface mapping electrode set assembly 21 to cardiac tissue.

Surface mapping electrode set assembly 21a illustrated in FIG. 5 has structural features that are substantially the same as those of the surface mapping electrode set assembly 21. In this embodiment, a finger sleeve 32 is mounted onto the head portion 24 and on the face thereof that is opposite to the administration surface 28. The finger sleeve 32 includes an opening 33 for receiving one or more fingers of the surgeon. By this structure, movement of the inserted finger(s) will impart a desired generally curved shape to the administration surface 28 in order to provide conformation to the shape of the heart tissue being mapped.

FIGS. 6 and 7 provide alternative-embodiment surface mapping electrode set assemblies 21b, 21c, each of which includes the ribbon wire arrangement of the surface mapping electrode set assembly 21. Each of these structures includes a flexible backing plate 34 mounted onto the head portion 24 at a location on the side thereof that is opposite to the administration surface 28. In FIG. 6, the flexible backing plate 34 is affixed directly onto the head portion 24 and provides all of the backing properties desired for this particular embodiment. Such backing properties are provided in order to enhance the ability of the head portion 24 to maintain the desired bend or curvature to an extent greater than can be maintained by the ribbon wire alone. Flexible backing plate 34 may be made of a biocompatible malleable metal, polymeric material or resin material. Surface mapping electrode set assembly 21c of FIG. 7 further includes a reinforcement plate 35 for further modifying the ability of the head portion 24 to retain a desired bent orientation.

While the surface mapping electrode set assemblies 21, 21a, 21b and 21c could be utilized for either epicardial or endocardial mapping, each is somewhat more advantageously used to achieve epicardial mapping. Surface mapping electrode set assemblies, generally designated as 41, 41a and 41b are especially suitable for endocarcial mapping, although each also can be utilized for epicardial mapping.

Surface mapping electrode set assembly 41 that is illustrated in FIGS. 8 and 9 includes a plurality of elongated wires 22 having insulation thereover. Such insulated wires 22 may be independent wires, although it has been found that overall handling of the surface mapping electrode set assembly 41 is usually enhanced if such are provided with a ribbon wire structure including the polymeric sheath 23 as previously described herein. A finger sleeve 42 is affixed to the insulated wires 22 in a convenient manner. Typically, the insulated wires 22 rest along a longitudinal inside surface of the finger sleeve 42 and may be adhered thereto. The distal tip 30 of each elongated wire 22 is embedded, generally within the distal end 43 of the finger sleeve 42. A slit 29 is made through an administration surface 40 of the distal end 43 at a location immediately above a portion of each elongated wire 22 and spaced from the distal tip 30 thereof. The portion of wire under the slit 29 is pulled through the slit in order to form each generally arcuate electrode 27.

Surface mapping electrode set assembly 41a of FIGS. 10 and 11 includes a ring 44, typically flexible, for receiving a finger or fingers of the surgeon. The ring 44 includes an administration surface 45 having slits 29 through which the generally arcuate electrodes 27 respectively protrude. Elongated wires 22 may be provided as generally discussed in connection with the embodiment of FIGS. 8 and 9. The distal tip 30 of each elongated wire 22 is embedded below the administration surface 45.

Surface mapping electrode set assembly 41b illustrated in FIGS. 12, 13 and 14 includes a pad 46 having slits 29 through which generally arcuate electrodes 27 project. This particular embodiment includes a handle 47 that provides enhanced reaching capabilities and is typically less flexible than handle portions 25 of the various other embodiments. Typically, such handle 47 will not take the form of a ribbon wire as previously discussed herein, although such is possible if desired. The particular structure illustrated in the drawings has a handle 47 having a cross-section that is substantially smaller than that of the pad 46. Handle 47 includes a plurality of elongated wires 22 and an armature 49 within an elongated tube 48.

By this structure, the individual elongated wires 22 are insulated from each other and, if necessary, from the armature 49. Armature 49 is a somewhat stiff, but hand-malleable material that can be bent as needed and that will retain its bent shape in response to forces developed during the mapping procedure, such as those imparted when the pad 46 contacts the portion of the heart being mapped. Armature 49 may, for example, be a relatively thick, soft, single-stranded wire, such as insulated copper. Any component of each of the surface mapping electrode set assemblies should be biocompatible, including the armature 49. This embodiment is particularly suitable for endocardial mapping since the thin pad 46 and a portion of the thinner handle 47 is readily inserted through a slit in the heart chamber and since the relatively stiff but malleable handle 47 enhances controlled directing and placement of the pad 46.

Typically, the elongated wires 22 of any of the embodiments are made of stainless steel, and they may be multiple-stranded or single-stranded. Usually, such electrodes have generally circular cross-sections, although other cross-sections are possible, including those that are generally rectangular in cross-section to provide flat-surfaced generally arcuate electrodes. Exemplary circular cross-sectioned, multiple-stranded wire would have a diameter of approximately 14/thousandths to 16/thousandths of an inch, while the generally arcuate electrodes 27 would have a height on the order of between about 25/thousandths and 30/thousandths of an inch. The various non-metallic components, including the polymeric sheath, the various head portions, handles, handle portions, administration surfaces, finger sleeves, and finger rings, must be made of biocompatible materials that exhibit adequate flexibility and some degree of resiliency in order to provide generally atraumatic surfaces. Exemplary materials include latex rubber, silastic tubing, polytetraflouroethylene (Teflon), polyvinylchloride, and the like.

It is to be appreciated that this invention can be embodied in various forms and therefore is to be construed and limited only by the scope of the appended claims.

I claim:

1. A surface mapping electrode set assembly comprising:
   a plurality of insulated elongated wires positioned generally longitudinally adjacent to each other, said plurality of elongated wires being included in both a head portion and a handle portion of the electrode set assembly;
   each said insulated wire having a distal end embedded within the head portion of the surface mapping electrode set;
   administration means on said head portion for contacting an organ to be mapped, said administration means including an insulated administration surface having a plurality of slits therethrough; and
   each said elongated wire having at least one non-intrusive electrode fixed relative to said administration surface, each said electrode being a generally arcuate section of the respective elongated wire, said generally arcuate wire electrode being located on said head portion of the surface mapping electrode set and being aligned generally parallel to the portion of said respective elongated wire adjacent said wire electrode, and each said generally arcuate wire electrode extending through one of said slits of the administration surface and projecting beyond the administration surface.

2. The surface mapping electrode set assembly according to claim 1, wherein each said generally arcuate wire electrode is a curved bend in the respective elongated wire.

3. The surface mapping electrode set assembly according to claim 1, wherein said head portion and said handle portion are bendable.

4. The surface mapping electrode set assembly according to claim 1, wherein said plurality of insulated wires comprise a ribbon electrode assembly including a unitary flexible polymeric sheath that generally encapsulates each of said elongated wires.

5. The surface mapping electrode set assembly according to claim 1, further including a finger sleeve mounted to said head portion onto a surface thereof that is opposite of said administration surface.

6. The surface mapping electrode set assembly according to claim 1, wherein said head portion includes a pad having the administration surface thereon, and wherein said handle portion includes an elongated tube within which said elongated wires are mounted.

7. The surface mapping electrode set assembly according to claim 6 further including a malleable armature within said elongated tube.

8. A surface mapping electrode set assembly comprising:
- a plurality of insulated elongated wires positioned generally longitudinally adjacent to each other, said plurality of elongated wires being included in both a head portion and a handle portion of the electrode set assembly;
- each said insulated wire having a distal end embedded within the head portion of the surface mapping electrode set;
- an insulated administration surface on said head portion, said insulated administration surface having a plurality of slits through its insulated surface;
- each said elongated wire having at least one non-intrusive electrode fixed relative to said administration surface, each said electrode being a generally arcuate section of the respective elongated wire, said generally arcuate wire electrode being located on said head portion of the surface mapping electrode set and being aligned generally parallel to the portion of said respective elongated wire adjacent said wire electrode, and each said generally arcuate wire electrode extending through one of said slits of the administration surface and projecting beyond the administration surface; and
- a flexible backing plate mounted to said head portion onto a surface thereof that is opposite of said administration surface.

9. The surface mapping electrode set assembly according to claim 8, further including a reinforcement plate between said head portion and said flexible backing plate.

10. The surface mapping electrode set assembly according to claim 1, further including a finger sleeve, and wherein said administration surface is at a distal end portion of said finger sleeve.

11. The surface mapping electrode set assembly according to claim 1, further including a ring member, and wherein said administration surface is on an outside surface of said ring member.

12. A method for providing a surface mapping electrode set assembly comprising:
- positioning a plurality of insulated, elongated wires generally longitudinally adjacent to each other;
- combining said plurality of insulated, elongated wires at a head portion having an insulated administration surface for contacting an organ to be mapped, said combining step including embedding the distal end of each insulated, elongated wire into the head portion;
- slitting the insulated administration surface at a location that overlies a short length of each of the elongated wires to thereby expose a plurality of uninsulated lengths of wire; and
- pulling each exposed length of wire through each slit in order to form a plurality of non-intrusive wire electrodes which are each a generally arcuate section of the wire and which project beyond the administration surface.

13. The method according to claim 12, wherein said slitting step includes locating the slit at a location proximally spaced from the embedded distal end of each elongated wire.

14. The method according to claim 12, wherein said pulling step includes inserting a hook-like tool within the slit and under the wire electrode portion at the slit.

15. The method according to claim 12, wherein said positioning step includes providing a ribbon electrode assembly including a unitary flexible polymeric sheath that generally encapsulates each of said elongated wires.

* * * * *

UNITED STATES PATENT AND TRADEMARK OFFICE
CERTIFICATE OF CORRECTION

PATENT NO. : 4,690,148

DATED : September 1, 1987

INVENTOR(S) : Stanley R. Hess

It is certified that error appears in the above-identified patent and that said Letters Patent is hereby corrected as shown below:

Under "References Cited U.S. PATENT DOCUMENTS", after "4,144,889  3/1979  Tyers et al. .......128/419 P X", insert --4,172,451  10/1979  Kline .......128/642--.
  Column 3, line 43, "heat" should read --head--.
  Column 6, line 15, "polytetraflouroethylene" should read --polytetrafluoroethylene--.
  Column 7, line 2, after "6", insert a comma, --,--.

Signed and Sealed this

Fourteenth Day of February, 1989

Attest:

DONALD J. QUIGG

Attesting Officer

Commissioner of Patents and Trademarks